(12) United States Patent
Ng et al.

(10) Patent No.: US 7,287,412 B2
(45) Date of Patent: Oct. 30, 2007

(54) METHOD AND APPARATUS FOR SENSING HYDROGEN GAS

(75) Inventors: Kwok Ng, San Jose, CA (US); Greg Monty, Libertyville, IL (US); Yunjun Li, Austin, TX (US); Zvi Yaniv, Austin, TX (US); Prabhu Soundarrajan, Austin, TX (US)

(73) Assignee: Nano-Proprietary, Inc., Austin, TX (US)

( * ) Notice: Subject to any disclaimer, the term of this patent is extended or adjusted under 35 U.S.C. 154(b) by 0 days.

(21) Appl. No.: 10/854,420

(22) Filed: May 26, 2004

(65) Prior Publication Data

US 2004/0261500 A1    Dec. 30, 2004

Related U.S. Application Data

(60) Provisional application No. 60/475,558, filed on Jun. 3, 2003.

(51) Int. Cl.
*G01N 27/04*  (2006.01)
*G01N 30/64*  (2006.01)
*G01N 33/22*  (2006.01)

(52) U.S. Cl. .................... 73/23.31; 73/31.05; 73/31.06

(58) Field of Classification Search ................ 73/23.2, 73/23.31, 23.32, 31.01, 31.02, 31.05, 31.06
See application file for complete search history.

(56) References Cited

U.S. PATENT DOCUMENTS

| | | | |
|---|---|---|---|
| 4,240,879 A | 12/1980 | Dobson | |
| 4,324,760 A | 4/1982 | Harris | |
| 5,670,115 A | 9/1997 | Cheng et al. | |
| 5,886,614 A | 3/1999 | Cheng et al. | |
| 6,103,540 A | 8/2000 | Russell et al. | |
| 6,120,835 A | 9/2000 | Perdieu | |
| 6,359,288 B1 | 3/2002 | Ying et al. | |
| 6,450,007 B1 | 9/2002 | O'Connor | |
| 6,465,132 B1 | 10/2002 | Jin | 429/231.8 |
| 6,525,461 B1 | 2/2003 | Iwasaki et al. | |
| 6,535,658 B1 | 3/2003 | Mendoza et al. | |
| 6,673,644 B2 * | 1/2004 | Gole et al. | 438/49 |
| 6,737,286 B2 | 5/2004 | Tao et al. | |
| 6,770,353 B1 * | 8/2004 | Mardilovich et al. | 428/209 |
| 6,788,453 B2 | 9/2004 | Banin et al. | |
| 6,849,911 B2 | 2/2005 | Monty et al. | |
| 6,882,051 B2 | 4/2005 | Majumdar et al. | |
| 2002/0079999 A1 | 6/2002 | Abdel-Tawab et al. | |

(Continued)

OTHER PUBLICATIONS

Minhee Yun et al., "Nanowire Growth for Sensor Arrays," to appear in *Nanofabrication Technologies*, Ed. E. A. Dobisz, SPIE Proceedings 5220, 2003, pp. 1-9.

(Continued)

*Primary Examiner*—Hezron Williams
*Assistant Examiner*—David A. Rogers
(74) *Attorney, Agent, or Firm*—Fish & Richardson, P.C.; Kelly Kordzik (57) ABSTRACT

A hydrogen sensor and/or switch fabricated from an array of nanowires or a nanoparticle thick film composed of metal or metal alloys. The sensor and/or switch demonstrates a wide operating temperature range and shortened response time due to fabrication materials and methods. The nanowires or nanoparticle thick films demonstrate an increase in conductivity in the presence of hydrogen.

12 Claims, 10 Drawing Sheets

U.S. PATENT DOCUMENTS

| | | | |
|---|---|---|---|
| 2002/0117659 A1 | 8/2002 | Lieber et al. | |
| 2002/0132361 A1 | 9/2002 | Vossmeyer et al. | 436/151 |
| 2003/0079999 A1 | 5/2003 | Penner et al. | 205/775 |
| 2003/0135971 A1 | 7/2003 | Liberman et al. | |
| 2003/0139003 A1 | 7/2003 | Gole et al. | 438/200 |
| 2003/0189202 A1 | 10/2003 | Li et al. | |
| 2004/0023428 A1 | 2/2004 | Gole et al. | 438/48 |
| 2004/0067646 A1 | 4/2004 | Tao et al. | |
| 2004/0070006 A1 | 4/2004 | Monty et al. | 257/200 |
| 2004/0071951 A1* | 4/2004 | Jin | 428/323 |
| 2004/0104129 A1* | 6/2004 | Gu et al. | 205/775 |
| 2004/0106203 A1* | 6/2004 | Stasiak et al. | 436/49 |
| 2004/0118698 A1* | 6/2004 | Lu et al. | 205/224 |
| 2005/0005675 A1 | 1/2005 | Monty et al. | |
| 2005/0072213 A1* | 4/2005 | Besnard et al. | 73/31.06 |

OTHER PUBLICATIONS

Frederic Favier et al., "Hydrogen Sensors and Switches from Electrodeposited Palladium Mesowire Arrays," *Science*, vol. 293, Sep. 21, 2001, pp. 2227-2231.

Favier et al., "Hydrogen Sensors and Switches from Electrodeposited Palladium Mesowire Arrays," *Science*, pp. vol. 293, Sep. 21, 2001, pp. 2227-2231.

Jayaraman, V., et al., "Synthesis and Hydrogen Permeation Properties of Ultrathin Palladim-Silver Alloy Membranes," *Journal of Membrane Science*, (104), 1995, pp. 251-262.

Keuler, J.N., et al. "Characterization of Electroless Plated Palladium-Silver Alloy Membranes," *Thin Sold Films*, 347: 1999, pp. 91-98.

Lewis, F.A., "A Comparison of the Properties of Palladium with Those of Other Transition Elements," The University of Texas Library, Academic Press 1967, pp. 1-31, 48-51, 56-57, 70-71, 74-79, 82-83, 86-87, 90-93, 112-113, 140-414, 144-142, and 160-161.

Oh, Chanick, et al., "$^1$H NMR Study of Hydrogen in Palladium Nanocrystals," *Journal of the Korean Physical Society*, vol. 43, No. 6, Dec. 2003, pp. L958-L962.

Suleiman, et al., "The Effect of the Cluster Structure in the Phase Transition During Hydrogen Absorption," Annual Reports of Deutsches Elektronen-Synchroton (DESY) (2002).

Suleiman, et al., "Pd-H Clusters: Non-Bulk Like Behaviour," Annual Reports of Deutsches Elektronen-Synchroton (DESY) (2003).

Tong, H.D., et al., "A Hydrogen Separation Module Based on Wafer-Scale Micromachined Palladium-Silver Alloy Membranes," *IEEE*, Transducers '03 The 12$^{th}$ International Conference on Solid State Sensors, Actuators and Microsystems, Boston, Jun. 8-12, 2003, pp. 1742-1745.

Walter, et al., "Sensors from Electrodeposited Metal Nanowires," *Surface and Interface Analysis*, 2002; 34: pp. 409-412.

Yun, Minhee, et al., "Nanowire Growth for Sensors Arrays," *Nanofabrication Technologies*, Ed. E.A. Dobisz, SPIE Proceedings 5220; Oct. 2003; pp. 1-9.

PCT Search Report for related application PCT/US03/27083; mailed May 27, 2004.

PCT Search Report for related application PCT/US04/17324; mailed Sep. 19, 2005.

* cited by examiner

METHOD AND APPARATUS FOR SENSING HYDROGEN GAS

CROSS-REFERENCE TO RELATED APPLICATIONS

The present invention claims priority to U.S. Provisional Application Ser. No. 60/475,558 filed Jun. 3, 2003.

TECHNICAL FIELD

The present invention relates to hydrogen gas sensors and, more particularly, to hydrogen gas sensors and switches that utilize metal nanowires.

BACKGROUND INFORMATION

Like any fuel, hydrogen stores large amounts of energy, and handling hydrogen requires safety precautions. As the use of hydrogen fuel becomes more common, there will be an increased need for reliable hydrogen sensors. Hydrogen is now used in the transportation, petrochemical, food processing, microchip, and spacecraft industries. Each of these industries needs reliable hydrogen sensors for many applications, for example, pinpointing leaks to prevent the possibility of explosions in production equipment, transport tanks, and storage tanks. Advances in fuel cell technology will provide numerous future applications for hydrogen sensors.

Hydrogen sensors, in some instances, could be used to warn of an imminent equipment failure. Electrical transformers and other electrical equipment are often filled with insulating oil to provide electrical insulation between energized parts. The presence of hydrogen in the insulating oil can indicate a failure or potential explosion. Hydrogen sensors could be utilized both under the insulating oil and in the air immediately above the insulating oil. Therefore, closely monitoring hydrogen levels in and around equipment containing insulating oil could be an effective tool in predicting and preventing equipment failure.

As fuel cell technology advances, fuel cells will see greater use as power sources for both vehicles and homes. Since hydrogen can be a highly explosive gas, each fuel cell system needs hydrogen detectors to sense and alarm in the event of a hydrogen leak. Hydrogen detectors can also be placed inside a fuel cell to monitor the health of the fuel cell. Hydrogen sensor packages are also needed to monitor hydrogen concentration in the feed gas to fuel cells for process control.

Hydrogen sensor packages in fuel cells require high sensitivity. Such sensor packages should have a wide measurement range spanning from below 1% up to 100% hydrogen. The measurement range is dependent on which fuel cell technology is used and the status of the fuel cell. Detectors are needed also to monitor for leaks in the delivery system. For transportation and other portable applications, hydrogen detectors operating in ambient air are needed to ensure the safety of hydrogen/air mixtures and to detect hydrogen leaks before they become a hazard. At high hydrogen concentration levels, issues associated with the potentially deteriorating effect on the oxygen pump operation must be addressed. Finally, hydrogen sensors must be highly selective in monitoring hydrogen in ambient air.

There are many commercially available hydrogen sensors, however, most of them are either very expensive or do not have a wide operating temperature range. Additionally, most sensors sold today have heaters included with the sensor to maintain elevated operating temperatures, requiring high power consumption that is undesirable for portable applications.

Favier et al. pioneered the use of palladium nanowires in 2001 by producing a demonstration hydrogen detector. The disclosure of Favier et al. can be read in an article published in Science, Vol. 293, Sep. 21, 2001. Hydrogen sensors prepared by this method have incredible properties due to the nature of the chemical/mechanical/electrical characteristics of the nanotechnology of palladium nanowires. The hydrogen sensors operate by measuring the conductivity of metal nanowires arrayed in parallel. In the presence of hydrogen gas, the conductivity of the metal nanowires increases.

The alpha-to-beta phase transition in the nanowire material is the mechanism for operation of these sensors. There is first a chemical absorption of hydrogen by the palladium nanocrystals of the nanowire. This causes expansion of the lattice by as much as 5-10%, causing the palladium nanocrystals that were initially isolated from each other to touch and form an excellent low-resistance wire.

However, there are many drawbacks to systems as produced and disclosed by Favier et al. A lack of complete characterization of the palladium nanowires has limited the understanding of those devices. Also, the Favier et al. method and apparatus utilizes nanowires that are electrochemically prepared by electrodepositon onto a stepped, conductive surface such as graphite. This presents a problem because nanowires prepared on conductive surfaces are required to be transferred off of the conductive surface so that the conductivity of the nanowire array can be measured more readily. Such transfers of nanowires cause degradation of hydrogen sensing at higher temperatures. In summary, the major issues with pure palladium nanowires prepared on step edges of graphite are: (1) unpredictable formation of palladium nanowires; (2) narrow temperature range of operation; and (3) narrow range of sensitivity to hydrogen concentration.

As a result, there is a need in the art for an apparatus and method for (1) predictably forming palladium and palladium alloy nanowires; (2) increasing the temperature operating range of sensors; and (3) increasing the range of hydrogen concentrations that can be measured.

SUMMARY OF THE INVENTION

The present invention is directed to an improved method and apparatus for sensing hydrogen gas. An embodiment comprises the steps of depositing an insulating layer onto a silicon substrate, depositing a metal layer on the top surface of the insulating layer, and depositing a plurality of nanoparticles onto the side-wall of the metal layer. In an embodiment, the metal layer may be removed.

Another embodiment of the present invention is directed to a hydrogen sensing apparatus comprising nanoparticles deposited on a substrate to form one or more nanoparticle paths which conduct electricity in the presence of hydrogen and wherein the nanoparticles were formed in close proximity to the substrate and not transferred off of a conductive substrate.

Another embodiment of the present invention is directed to a method of sensing hydrogen including depositing a first layer of material onto a second layer of material, depositing a metal layer on the second layer of material, depositing a third layer of material on the metal layer, removing a portion of the metal layer to expose one or more side-walls of the metal layer, depositing nanoparticles on the side-walls of the metal layer, and sensing a change of resistivity of the nanoparticles when they are exposed to hydrogen.

An embodiment of the present invention is directed to a palladium-silver alloy nanowire technology that eliminates the (1) unpredictable formation of palladium nanowires; (2) narrow temperature range of operation; and (3) narrow range of sensitivity to hydrogen concentration. A basis of the present invention is the ability to co-deposit palladium and palladium-silver alloy nanoparticles or nanowires electrochemically on a patterned surface without the need for a transfer process.

The present invention operates by measuring the resistance of many metal nanowires arrayed in parallel in the presence of hydrogen gas. The present invention may also operate by, in the presence of hydrogen, measuring the resistance of nanowires deposited as a film. The nanowires or nanofilm contain gaps that function as open switches in the absence of hydrogen. In the presence of hydrogen, the gaps close and behave like closed switches. Therefore, the resistance across an array of palladium or palladium alloy nanowires or nanofilm is high in the absence of hydrogen and low in the presence of hydrogen.

The nanowires or nanofilm are typically composed of palladium and its alloys. One of ordinary skill recognizes that any other metal or metal alloy having a stable metal hydride phase such as copper, gold, nickel, platinum and the like may also be used. Herein the use of the term "path" is meant to encompass nanowires, nanofilm, and/or any potentially electrically conductive path.

In the prior art, nanowires were electrochemically prepared by electrodepositon onto a stepped surface such as graphite. The nanowires were then transferred off of the graphite onto a polystyrene or cyanoacrylate film. The transfer process contributed to a decrease in sensitivity and operating range for hydrogen sensors. It is an object of the present invention to increase sensitivity and operating range of the hydrogen sensors by dispensing with the need to transfer nanowires during fabrication.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

In the following description, numerous specific details are set forth such as specific alloy combinations, etc. to provide a thorough understanding of the present invention. However, it will be obvious to those skilled in the art that the present invention may be practiced without such specific details. Some details have been omitted in as much as such details are not necessary to obtain a complete understanding of the present invention and are within the skills of persons of ordinary skill in the relevant art.

Refer now to the drawings wherein depicted elements are not necessarily shown to scale and wherein like or similar elements are designated by the same reference numeral through the several views.

The present invention is directed to an improved apparatus and method for sensing hydrogen gas. The addition of silver to the palladium nanowires significantly increases the operating temperature range of the sensor. The incorporation of silver with palladium also addresses the issue of sensitivity of the nanowires to different levels of hydrogen concentrations. Pure palladium nanowires typically do not provide enough sensitivity to allow detection over a large range of hydrogen concentrations. At room temperature, pure palladium nanowires are able to detect a concentration of about 2% hydrogen. At higher temperatures, pure palladium wires require a higher concentration of hydrogen for detection. However, the incorporation of silver in palladium nanowires provides a greater range of detection suitable to make hydrogen sensors.

Figure 1:
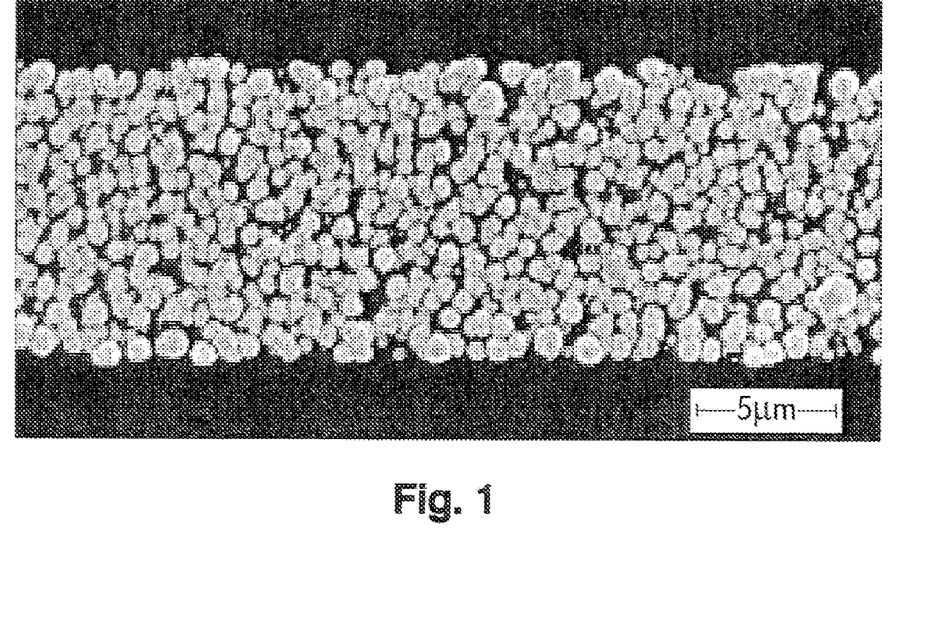
FIG. 1 is an image from a scanning electron microscope (SEM) of a nanoparticle thin film.
Figure 2:
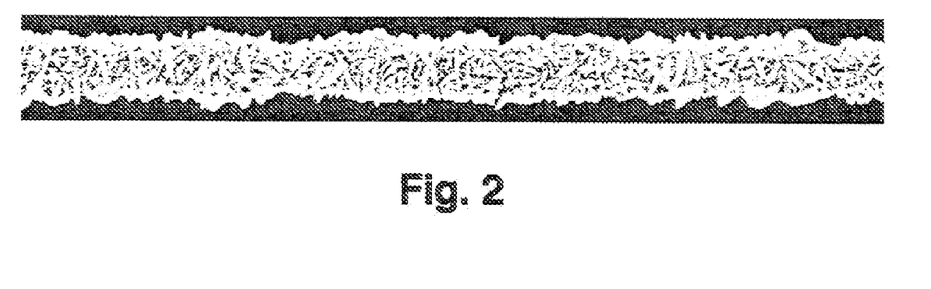
FIG. 2 is an SEM image of 300 nm palladium nanowires prepared by side-wall-electroplating technique.

The substrate for an embodiment can be any insulating surface such as polymer, glass, silicon, or silicon nitride. A thin layer of titanium is deposited onto the substrate to form a conductive area for electroplating. A photoresist pattern is prepared on the top of the substrate by lithography. Palladium or palladium-silver alloy nanoparticles/nanowires are then electroplated on the exposed titanium surface. The palladium electroplating bath contains 1 mM $PdCl_2$, 0.1 M HCl in water. The palladium-silver electroplating bath contains 0.8 mM $PdCl_2$, 0.2 mM $AgNO_3$, 0.1 M HCl, 0.1 M $NaNO_3$, and 2 M NaCl in deionized water. The nanoparticles/nanowires are deposited at −50 mV vs SCE for 600 sec with one second large overpotential pulse (−500 mV vs SCE). FIG. 1 shows an image of a nanoparticle thin film that consists of nanoparticles with a 100 nm diameter. FIG. 2 shows an image of 300 nm palladium nanowires prepared by side wall technique.

Figure 3:
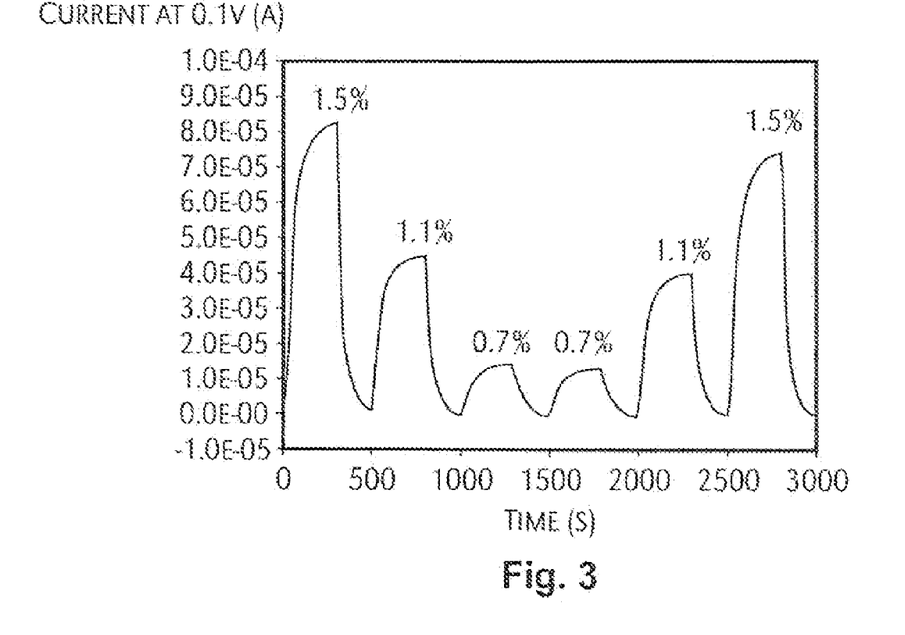
FIG. 3 is a graph of hydrogen sensor responses at varying hydrogen concentrations at 70° C.
Figure 4:
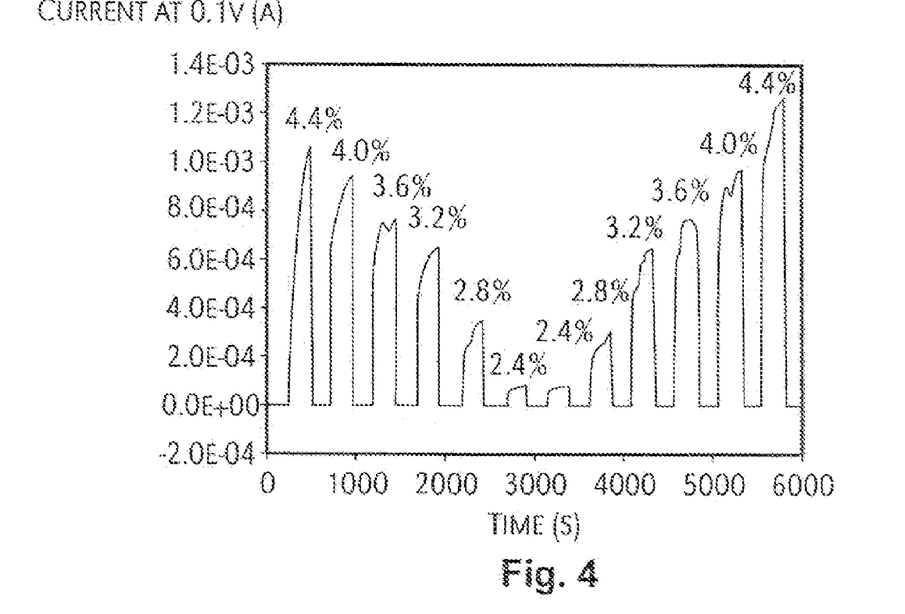
FIG. 4 is a graph of hydrogen sensor responses at varying hydrogen concentrations at 70° C.

FIG. 3 and FIG. 4 show the response of a palladium-silver alloy hydrogen sensor at 70° C. for varying hydrogen concentrations over time. Note that the devices are essentially OFF when no hydrogen is present and palladium alloy-nanocrystals in the device act as an "open circuit" with very-high resistance. When the device is exposed to hydrogen, the palladium alloy-nanocrystals in the device touch each other through expansion of the lattice. This causes any nanogaps in the wires to close (ON state) and the nanowires behave as a "short circuit" with very-low resistance. The sensors have a highly desirable characteristic in that the sensors require essentially zero power in the absence of hydrogen. The sensor acts like an open circuit in the absence of hydrogen and only draws a small amount of power when an alarm condition occurs. This is the ideal situation for a good hydrogen detector: OFF in the absence of hydrogen, and ON only when hydrogen is present.

Figure 5A:
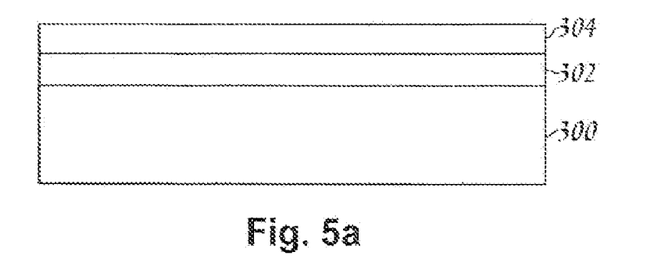
FIG. 5a is a schematic representation of one embodiment of the present invention.
Figure 5B:
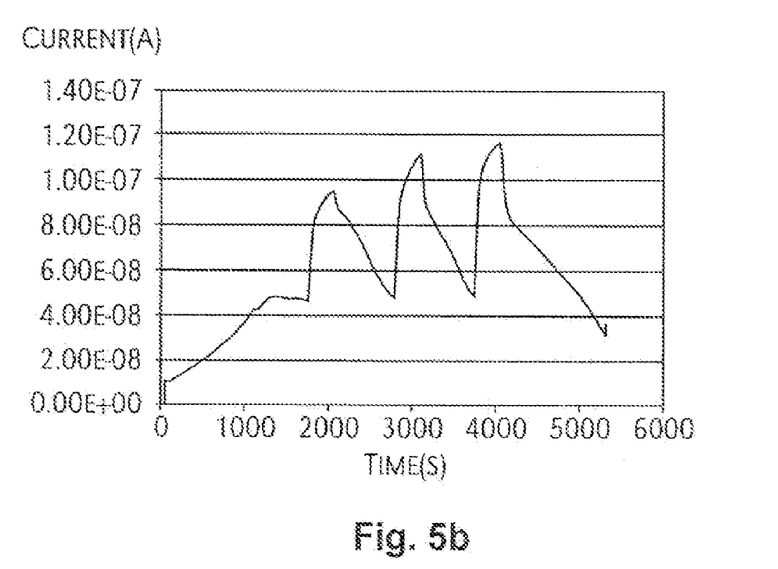
FIG. 5b is a graph of hydrogen sensor responses at 100° C. with hydrogen concentrations of 0.5%, 1.5%, and 2%.
Figure 5C:
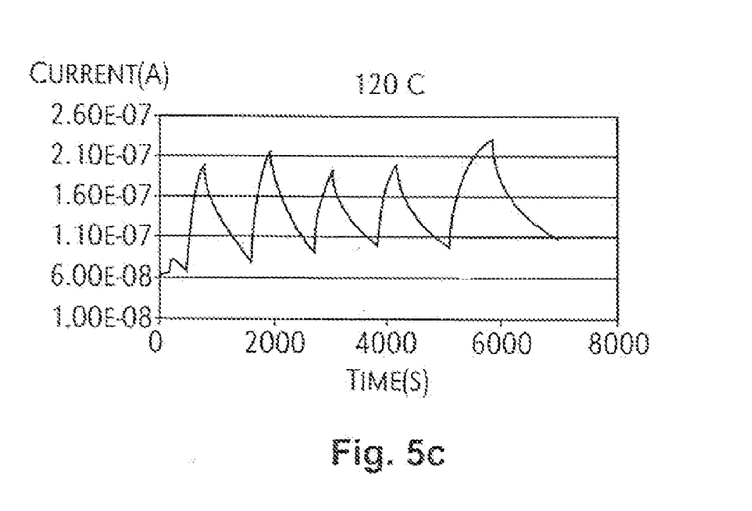
FIG. 5c is a graph of hydrogen sensor responses during 5 cycles of testing at 1% hydrogen concentration at 120° C.

Turning to FIG. 5a, a particular embodiment of making a hydrogen sensor involves evaporating a 1000 Å layer 302 of titanium onto a polymide film 300 such as Kapton. One of ordinary skill in the art will recognize that any insulating material such as glass or silicon may be substituted for Kapton. Next, a photoresist (not shown) is patterned on the titanium layer 302 in a well-known manner. A layer 304 of nanoparticles of palladium-silver alloy are then electroplated onto the surface. The device is heated to 500° C. for 2 hours in air to oxidize the titanium layer. FIG. 5b displays test results for this embodiment at 100° C. In this test, an exemplary sensor of the instant embodiment was tested for 3 cycles with hydrogen concentrations of 0.5%, 1.5%, and 2%. FIG. 5c displays results for tests at 120° C. with 1% hydrogen concentrations. FIG. 5c illustrates that the sensor did not degrade after 5 cycling tests.

Figure 6A:
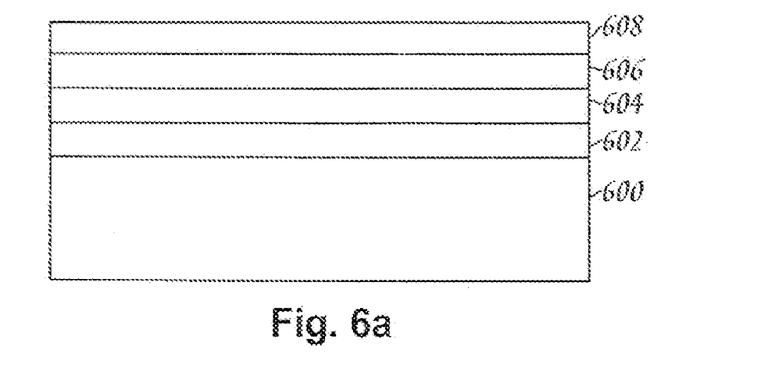
FIG. 6a is a schematic representation of one embodiment of the present invention.

Another embodiment of the present invention is depicted schematically in FIG. 6a. In this embodiment, a 5000 Å layer 602 of SiNx is deposited on a silicon substrate 600. A layer 604 of 1000 Å thick titanium is then deposited on layer 602. Using lithography, a pattern (not shown) is created on the substrate. A thin film 606 of palladium-silver nanoparticles is electroplated to layer 604. In one example of the instant embodiment, the palladium-silver alloy was electroplated at 300 μA for 1 second and 20 μA for 600 seconds. Next, oxidizing the titanium 604 forms $TiO_2$. In one example, the titanium was exposed to 500° C. air overnight. Following oxidation of the titanium, another layer 608 of palladium-silver is deposited to layer 606. In one example, palladium-silver was electroplated at 300 μA for 1 second and 20 μA for 200 seconds.

Figure 6B:
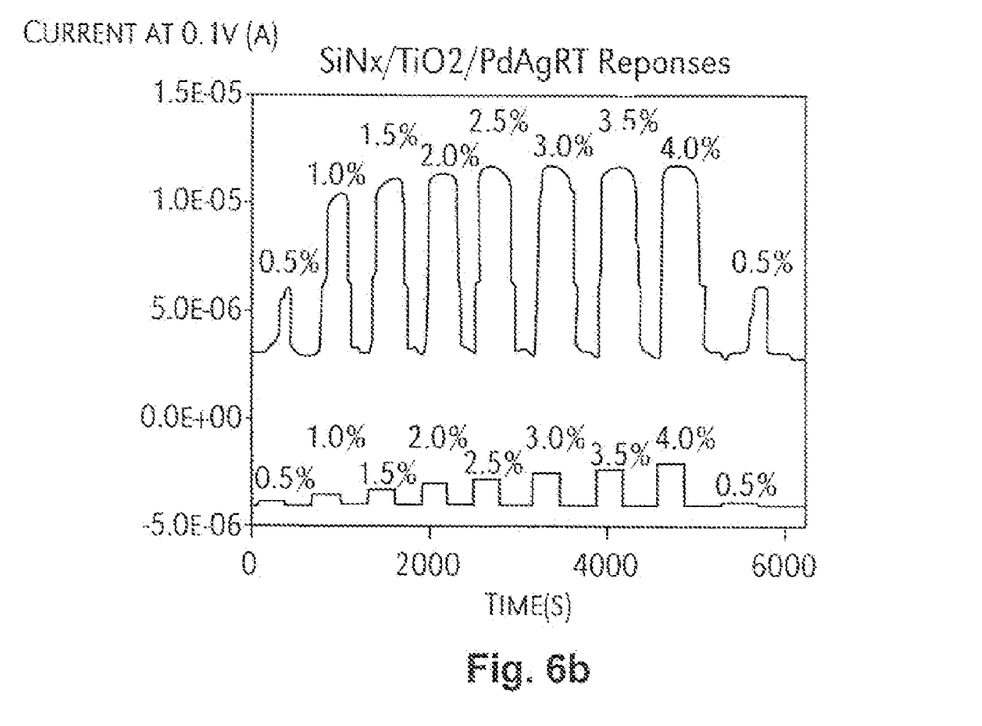
FIG. 6b is a graph of responses for the hydrogen sensor from FIG. 6a at room temperature at varying levels of hydrogen as shown.
Figure 6C:
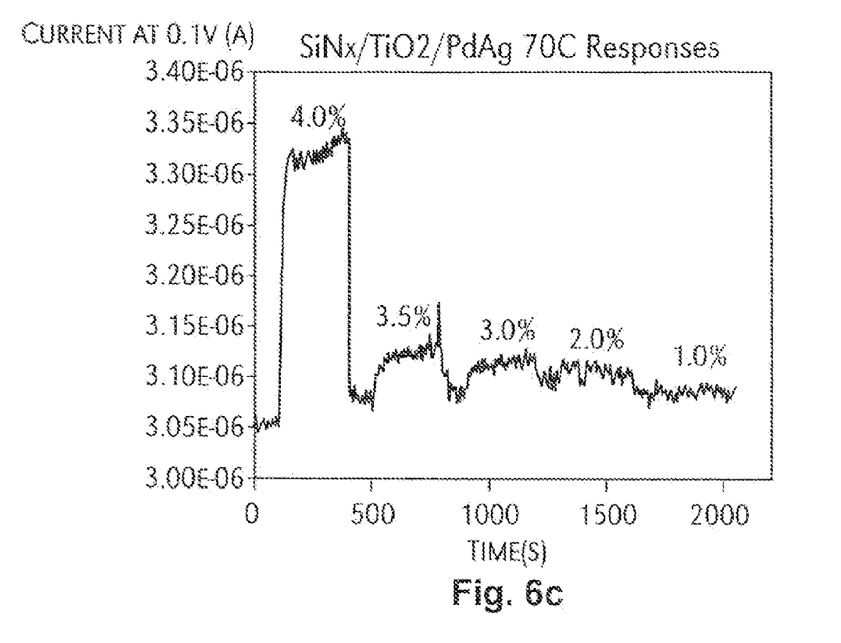
FIG. 6c is a graph of responses for the hydrogen sensor from FIG. 6a at 70° C. at varying levels of hydrogen as shown.
Figure 6D:
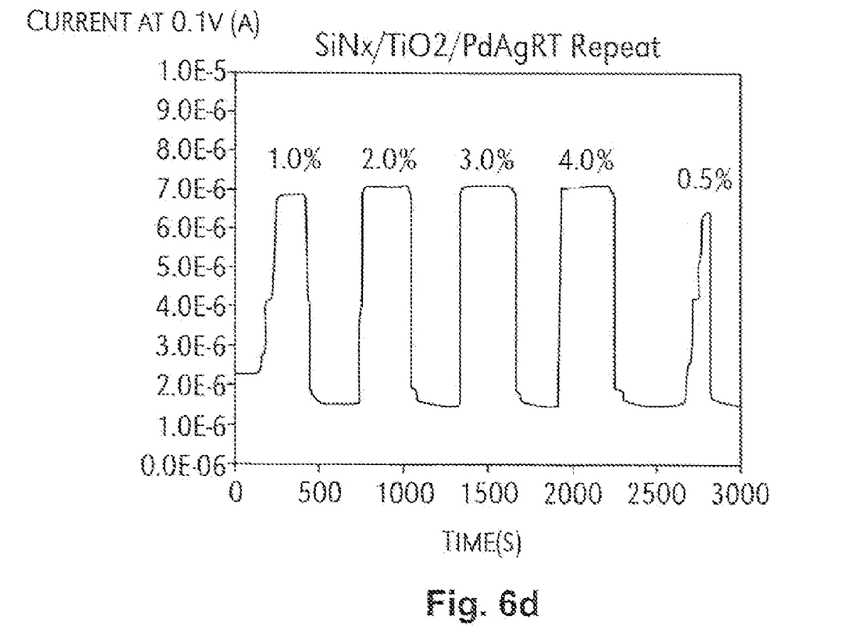
FIG. 6d is a graph of responses for the hydrogen sensor from FIG. 6a at room temperature at varying levels of hydrogen as shown.

FIGS. 6b-6d illustrate results achieved by testing the exemplary embodiment as depicted in FIG. 6a. FIG. 6b illustrates test results performed at room temperature. The device was first tested at room temperature with hydrogen concentrations ranging from 0.5% to 4%. The voltage applied was 0.1V. The current was about 3E-6A with no hydrogen present. The current rose to 7E-6A at 0.5% hydrogen and 1E-5A at 1% hydrogen. The response was slowly saturated at around 3% hydrogen concentration with a current of 1.2E-5A, about 400% of the current at OFF state.

FIG. 6c illustrates test results performed at 70° C. for the exemplary embodiment as depicted in FIG. 6a. At 120° C., the sensor did not respond to hydrogen. The results shown in FIG. 6c were achieved after slowly reducing the temperature from 120° C. to 70° C. FIG. 6c illustrates that the sensor was essentially non-operational when the temperature was raised to 120° C., but the sensor regained its operation when the temperature was reduced to 70° C.

FIG. 6d illustrates test results for the embodiment depicted in FIG. 6a after cooling the device from 70° C. to room temperature. The device responded to hydrogen with similar magnitude as the previous test at room temperature, illustrated in FIG. 6b. In the OFF state, the device had a current of about 1.5E-6A. In the ON state, the current was about 7E-6A at 4% hydrogen. This result showed about 400% change in magnitude between OFF and ON states. The difference in current of the OFF state before and after high temperature testing might indicate some degradation, but the relative changed in resistance (400%) was about the same.

The embodiment depicted in FIG. 6a provides a way to prepare a hydrogen sensor without using the transfer method. However, unlike using Kapton, the tested device did not work at 120° C. In fact, the sensitivity of the sensor decreased as the temperature increased. Nevertheless, the sensor showed good sensitivity at room temperature with more stable and less noisy response curves.

Figure 7A:
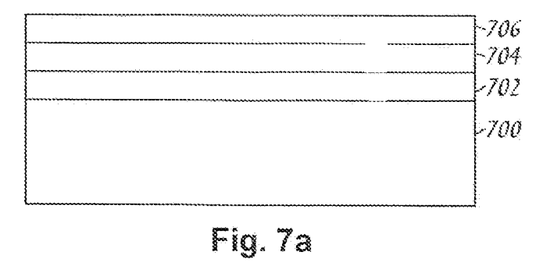
FIG. 7a is a schematic representation of another embodiment of the present invention.
Figure 7B:
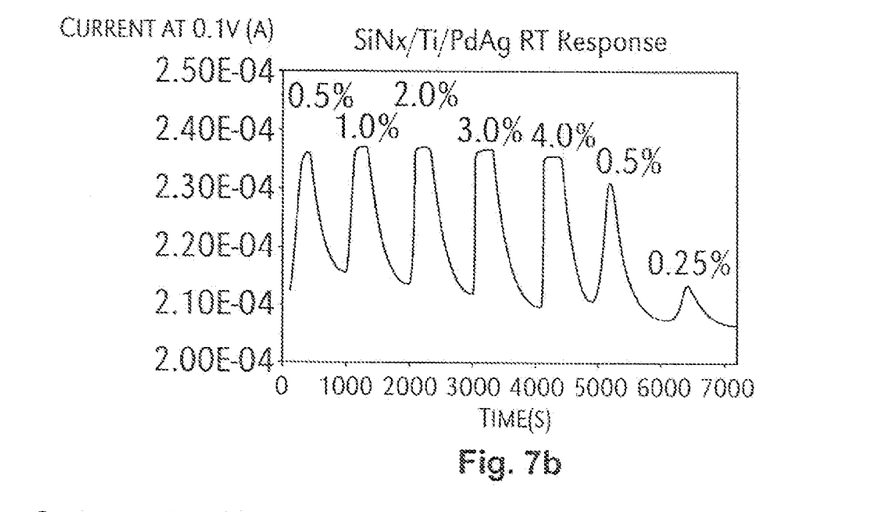
FIG. 7b is a graph of responses for the hydrogen sensor from FIG. 7a at room temperature at varying levels of hydrogen as shown.
Figure 7C:
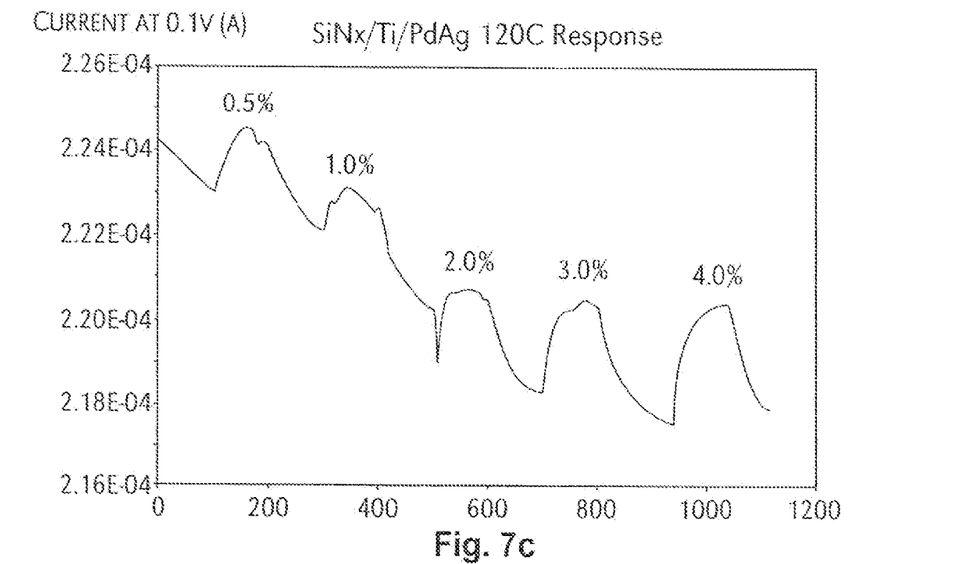
FIG. 7c is a graph of responses for the hydrogen sensor from FIG. 7a at 120° at varying levels of hydrogen as shown.

Another embodiment of the present invention is shown schematically in FIG. 7a. FIG. 7a shows a silicon substrate 700 deposited with 5000 Å of SiNx, forming layer 702. Next, 200 Å of titanium is deposited to form layer 704. A layer 706 of palladium-silver is electroplated to titanium layer 704. In an example of the instant embodiment, palladium-silver was electroplated at 300 μA for 1 second and 20 μA for 600 seconds. Test results of an example of the instant embodiment are illustrated in FIG. 7b. The results in FIG. 7b were achieved at room temperature. A second experiment performed at 120° C. yielded the results shown in FIG. 7c. Although at 120° C. the change between OFF state to ON state was not very large, the device from this embodiment was able to detect hydrogen at 0.5% concentration both at room temperature and 120° C.

Figure 8A:
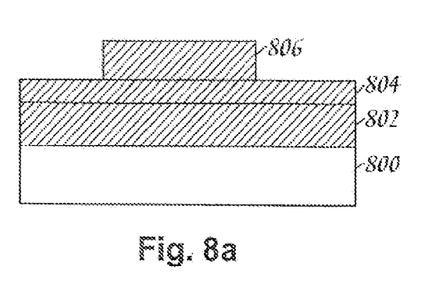
FIG. 8a is a schematic representation of an early stage of fabrication of an embodiment of the present invention.
Figure 8B:
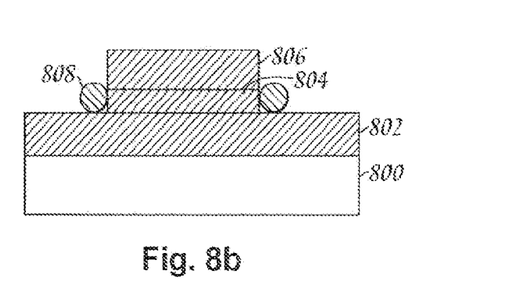
FIG. 8b is a schematic representation of an intermediate stage of fabrication of an embodiment of the present invention.
Figure 8C:
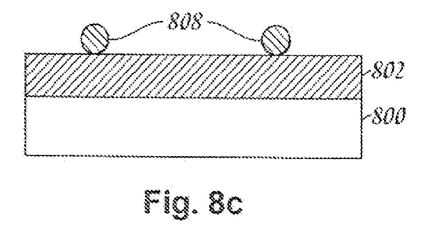
FIG. 8c is a schematic representation of a final stage of fabrication of an embodiment of the present invention.

Another embodiment of the present invention is depicted schematically in FIGS. 8a-8e. In this embodiment, $SiO_2$ is deposited on a silicon substrate 800 to form a 5000 Å layer 802 of $SiO_2$ One of ordinary skill in the art recognizes that SiNx or other suitable materials may be substituted for $SiO_2$. Titanium 200 Å thick is deposited to form layer 804. Next, the photoresist 806 is deposited on the substrate and patterned by photolithography leaving the assembly substantially as depicted in FIG. 8b, with layer 804 having two side-walls. Nanowires 808 made from palladium-silver alloys are then electroplated onto the side-walls of the titanium 804. In one example of the instant embodiment, palladium-silver was electroplated using a side-wall plating technique at 300 μA for 1 second and 20 μA for 600 seconds. Since the sidewall of the metal is the only place exposed to the electrolytic bath, the palladium-silver will be deposited on the sidewall only and form the nanowires at the edge of the metal lines. Next, the remaining titanium 804 is etched away, leaving the assembly as shown in FIG. 8c. Alternatively, the titanium 804 could be oxidized at high temperature or left on the substrate. The sensor is functional without removing the metal layer, but has a low S/N ratio. The removal of the metal layer provides higher S/N ratio.

The side-wall plating technique for an embodiment as shown in FIG. 8(c) and operational at high temperatures can be accomplished as follows: the substrate can be used as a working electrode in a three-electrode plating system with a saturated calomel electrode (SCE) as the reference electrode and platinum wire as the counter electrode. Using conventional electrochemical deposition/plating, the three electrodes can be immersed in a palladium silver alloy plating solution bath solution consisting of 2.5 mM of $PdCl2$, 0.5 mM of $AgNO_3$, 0.05 M of $NaNO_3$, 0.05 M of HCl, and 2 M (20 g in 100 mL) of NaCl in water. A standard electrochemical program, namely chronopotentiometry can be used for this process. For formation of the nanowires on the substrate, the electrochemical plating conditions can be as follows: using a pure palladium plating bath, apply $-300$ µA for 10 sec, then apply $-20$ µA for 450 sec. After electroplating, the substrate can be immersed in acetone, followed by IPA and water to remove the photoresist on the surface.

The side-wall plating technique for an embodiment as shown in FIG. 8(c) and operational at room temperature can be accomplished as follows: the substrate can be used as a working electrode in a three-electrode plating system with a saturated calomel electrode (SCE) as the reference electrode and platinum wire as the counter electrode. Using conventional electrochemical deposition/plating, the three electrodes can be immersed in a pure palladium plating bath consisting of 1 mM of $PdCl_2$ and 0.1 M HCl in water. A standard electrochemical program, namely chronopotentiometry can be used for this process. For formation of the nanowires on the substrate, the electrochemical plating conditions can be as follows: using pure palladium plating bath, apply $-300$ µA for 10 sec, then apply $-20$ µA for 450 sec. After electroplating, the substrate can be immersed in acetone, followed by IPA and water to remove the photoresist on the surface.

Figure 8D:
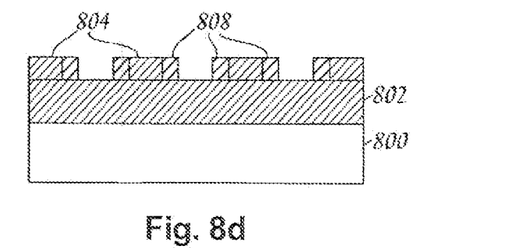
FIG. 8d is a schematic representation of an embodiment of the present invention configured into an array of nanowires.

FIG. 8d depicts an embodiment created by patterning the substrate using photolithography to electroplate multiple nanowires 808 to the side-walls of titanium strips 804. FIG. 8(d) is made in the similar fashion as outlined in 8(a) to 8(c); however, FIG. 8(d) shows multiple nanowires arranged in an array. A hydrogen sensor is utilized by connecting conductors to the ends of the array of nanowires which electrically connects the nanowires in parallel. In an embodiment, silver paste is applied to the ends of the array of nanowires and separate wires are connected to the silver paste on each end. A voltage is then applied across the parallel nanowires, and the resultant current is measured to determine whether there is hydrogen present. Using palladium-silver alloy nanowires, the current is higher in the presence of hydrogen than in the absence of hydrogen.

The particular embodiment as described in FIG. 8d can be fabricated as follows: 5000 Å $SiO_2$, item 802, is deposited on a 4 inch silicon wafer, item 800, using a E-beam evaporator followed by a layer of 200 Å titanium, item 804. The substrate is then coated with a photoresist hexamethylenedisilane (HMDS) for 30 seconds at 700 RPM followed by a positive photoresist for 90 seconds at 3000 RPM. The substrate is then exposed under UV light with a homemade H-Sensor 5 mm line mask (not shown) for 25 sec and further developed by photoresist developer diluted for 40 seconds. The substrate is then rinsed with water for 30 minutes, dried using a blow drier, and heated in an oven for 10 minutes at 120° C. The titanium layer not covered by the photo resist is then etched away by a titanium etchant, exposing the sidewall of the titanium layer over the entire substrate. The pattern is exposed under UV with homemade mask (not shown) for 25 seconds after proper alignment of the sensor pattern. The substrate is then developed by 400 K developer diluted for 40 seconds. The substrate is then rinsed with water for 30 minutes, dried using a blow drier, and heated in an oven for 10 minutes at 120° C.

The sidewall plating technique is then used to electroplate the nanoparticles 808 onto the substrate. After electroplating, the substrate is immersed in acetone followed by IPA and water to remove the photoresist from the surface. In an embodiment, the nanowires 808 are separated from the titanium 804 without removing them from 802.

Figure 8E:
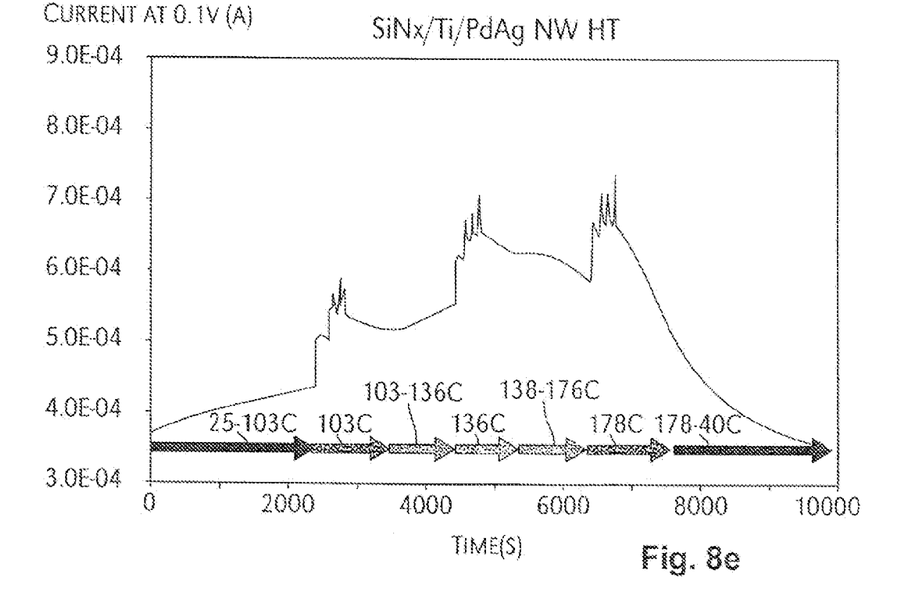
FIG. 8e is a graph of test results from an embodiment of the present invention tested at varying hydrogen levels and 103° C., 136° C. and 178° C.

FIG. 8e shows the results from testing an example of the embodiment as depicted in FIG. 8c. The test began at room temperature. The temperature was increased to 103° C., then 136° C., and then 178° C. As the temperature increased, the current increased due to the larger thermal expansion coefficient of palladium-silver compared to SiNx. The palladium-silver nanowires 808 expanded faster than the substrate and the resistance lowered. With the test chamber at 103° C., the sensor was tested with hydrogen concentrations of 0.25%, 1.0%, and 4.0%. As FIG. 8e shows, the sensor responded to each concentration level. The device was functional even at 178° C.

Figure 9A:
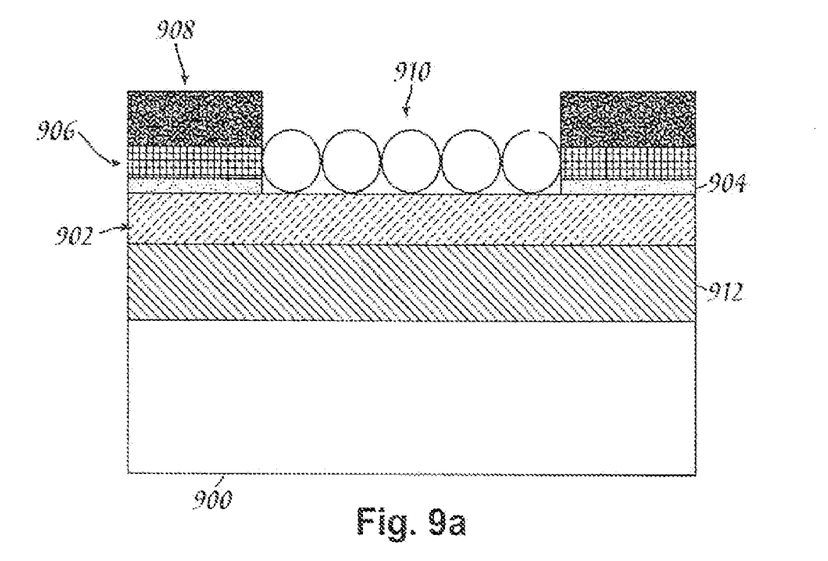
FIG. 9 is a schematic representation of an embodiment of the present invention.
Figure 9B:
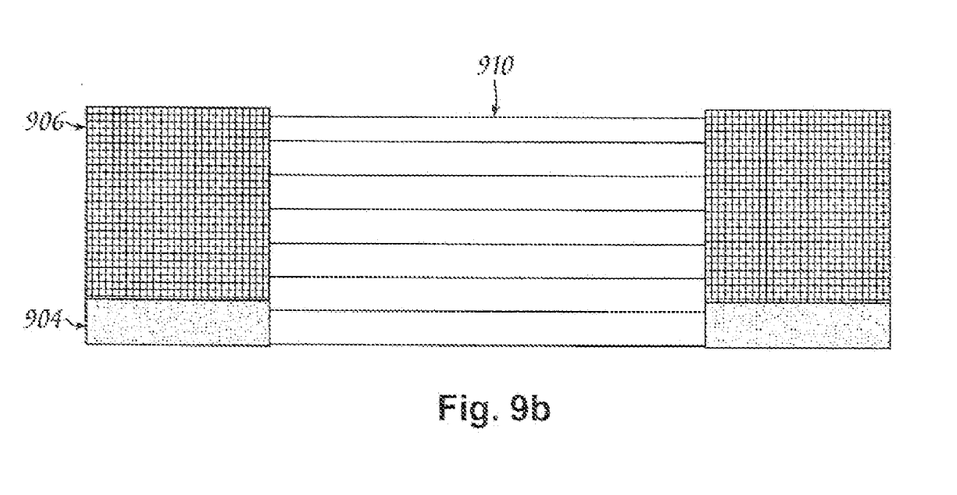

FIG. 9a-9b depicts another embodiment of the present invention. The embodiment of FIG. 9a-9b produces response curves typical of other embodiments described herein, but the embodiment in FIG. 9a-9b is suitable for fabricating hydrogen sensors to be operable both in ambient air and under oil, such as transformer oil.

The embodiment of FIG. 9a-9b can be fabricated using photolithography as follows: First, a 5000 Å layer 912 of silicon nitride is deposited on a 4 inch silicon wafer 900 using a E-beam evaporator followed by a layer 902 of 200 Å titanium. The substrate is then coated with a photoresist hexamethylenedisilane (HMDS) for 30 seconds at 700 RPM followed by a positive photoresist for 90 seconds at 3000 RPM. The substrate is then exposed under UV light with homemade H-Sensor 5 mm line mask (not shown) for 25 sec and further developed by photoresist developer diluted for 40 seconds. The substrate is then rinsed with water for 30 minutes, dried using a blow drier, and heated in an oven for 10 minutes at 120° C. A layer 904 of 100 Å chromium and 300 Å gold, item 906, is deposited using E-Beam. In an embodiment, the resistance of the substrate can be measured to be less than 10 ohms. The photoresist is lifted off using appropriate stripper followed by heating in oven for 30 minutes at 90° C. and subsequent drying.

The substrate is then coated with a photo resist 908 for 30 seconds at 700 RPM followed by positive photoresist for 90 seconds at 3000 RPM. The pattern is exposed under UV with homemade mask (not shown) for 25 seconds after proper alignment of the sensor pattern. The substrate is then developed by photoresist developer diluted for 40 seconds. The substrate is then rinsed with water for 30 min, dried using a blow drier, and heated in an oven for 10 minutes at 120° C. A plating technique is then used to electroplate the nanoparticles 910 onto the substrate. Note, in an embodiment the sidewall plating technique is not used because the titanium is not etched in this process. After electroplating, the substrate was immersed in acetone, followed by IPA and water to remove the photoresist on the surface.

Figure 10A:
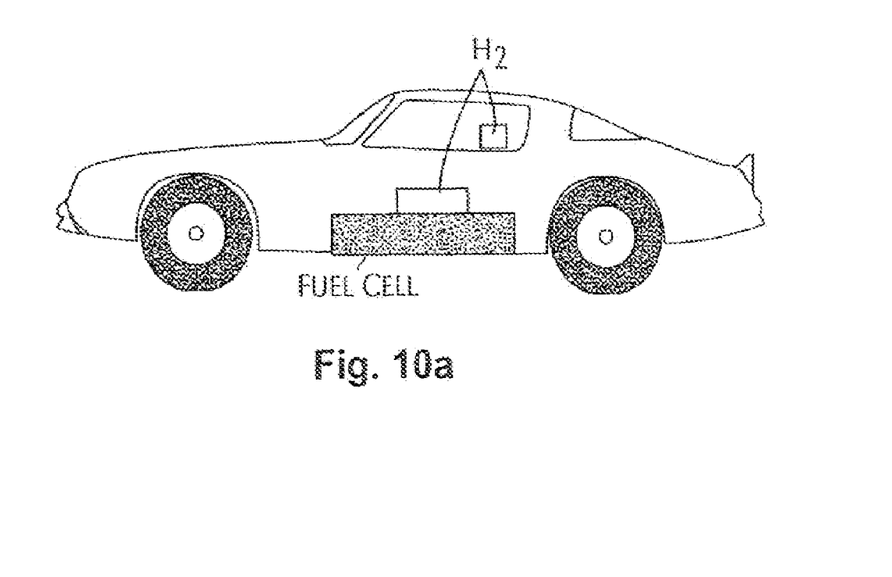
FIG. 10a is an illustration of hydrogen sensors used for automobile applications.
Figure 10B:
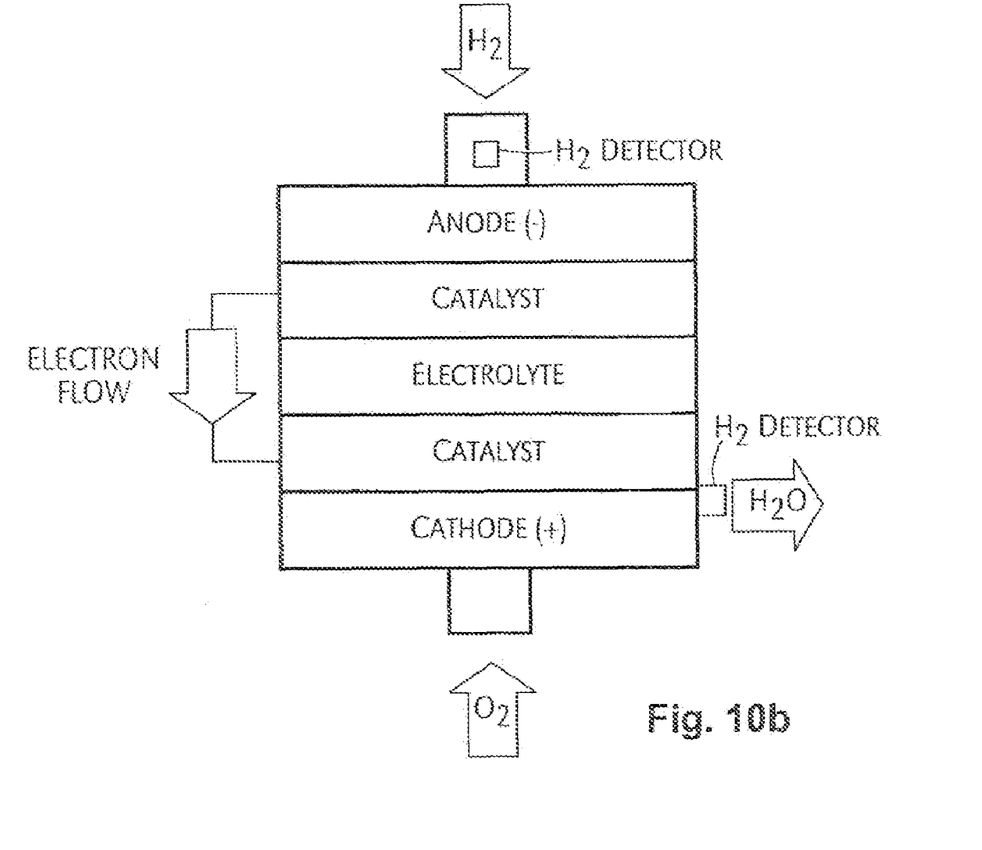
FIG. 10b is an illustration of hydrogen sensors within a fuel cell.

FIGS. 10a-10d show various applications for the present invention. FIG. 10a depicts an application for utilizing hydrogen sensors to monitor hydrogen levels inside a vehicle and within a fuel cell. Sensors in the vehicle cabin monitor to ensure that dangerous concentrations of hydrogen do not create an unsafe condition for drivers and passengers. Sensors within the fuel cell ensure proper operation and health of the fuel cell. FIG. 10b represents a fuel cell used to monitor the health of the fuel cell. The hydrogen sensor is placed to ensure proper hydrogen levels in the intake and to monitor the hydrogen level in the exhaust.

Figure 10C:
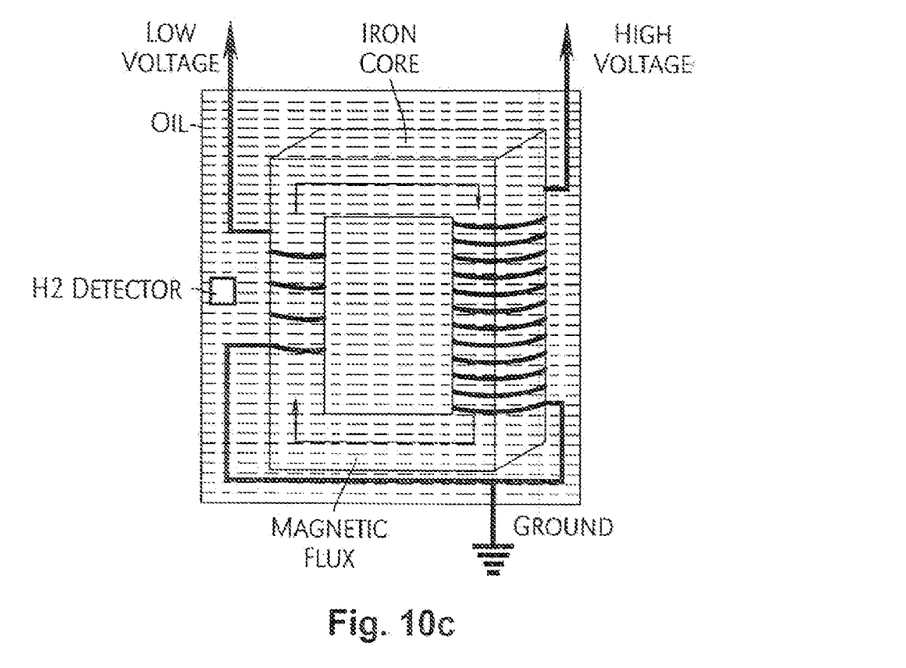
FIG. 10c is an illustration of hydrogen sensors used for transformer applications.
Figure 10D:
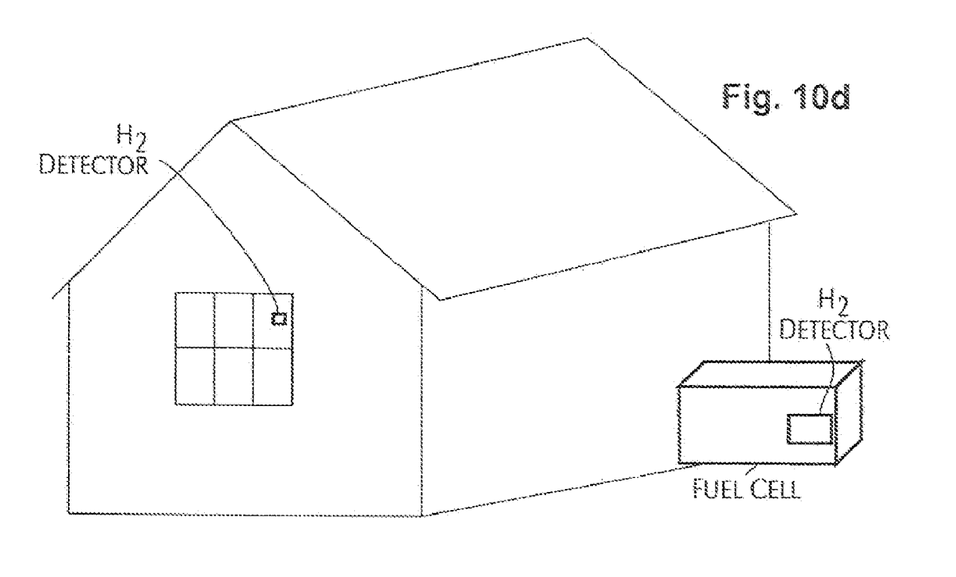
FIG. 10d is an illustration of hydrogen sensors used for home applications.

Similarly, FIG. 10d depicts an application for monitoring hydrogen concentration in and around a home utilizing a fuel cell. Hydrogen sensors in the home monitor for dangerous levels of hydrogen to protect occupants by preventing explosive buildups of hydrogen.

FIG. 10c depicts yet another application for hydrogen sensors in power equipment. As discussed previously, power transformers and switching equipment are often filled with insulating oil. A breakdown or contamination of the insulating oil can cause short circuits and lead to dangerous explosions and fires. Some potential failures are predicted by monitoring for buildups of hydrogen and other gases in the transformer oil. FIG. 10c shows a hydrogen sensor placed under the insulating oil of a transformer. Another sensor could be placed above the oil to monitor hydrogen levels. One of ordinary skill in the art recognizes that hydrogen sensors may also be placed in any application where a buildup of hydrogen signals a dangerous condition.

The present invention relates to using palladium-silver alloy thin film (or array, network) and nano/meso wires as an active element for hydrogen sensing applications. Embodiments of the present invention can detect 0.25% hydrogen in nitrogen. With the present invention, by preparing a very thin layer of metal (for example, titanium) or oxidizing a titanium layer to $TiO_2$ and preparing conductive palladium or palladium-silver nanostructures on the less conductive titanium or $TiO_2$ surface, there is no need for the transfer process which caused degradation of the sensor at high temperature. Test results show that palladium or palladium-silver nanoparticles (or nanowires) on titanium (or $TiO_2$) can be used to detect very low concentration (0.25%) of hydrogen at very high temperature (178° C.).

Although the present invention and its advantages have been described in detail, it should be understood that various changes, substitutions and alterations can be made herein without departing from the spirit and scope of the invention as defined by the appended claims.

What is claimed is:

1. An apparatus for sensing hydrogen comprising:
a substrate comprising an insulating material;
a conductive patterned layer deposited on the substrate; and
a plurality of nanoparticles comprising palladium deposited on the conductive patterned layer, wherein the conductive patterned layer is oxidized to form a resistive layer;
wherein some of the nanoparticles and portions of the resistive layer from at least one conductive path in the presence of hydrogen.

2. The apparatus of claim 1 wherein the at least one conductive path is formed by at least one nanowire.

3. The apparatus of claim 1 wherein the conductive patterned layer has a side wall, and the plurality of nanoparticles are deposited to the side-wall.

4. The apparatus of claim 1 wherein the substrate is composed of SiNx.

5. The apparatus of claim 1 wherein the substrate is composed of $SiO_2$.

6. The apparatus of claim 1, wherein, when in use, electrical conductivity in the presence of the at least one nanoparticle path is readily discernable over electrical conductivity of the substrate due to the non-conductive nature of the substrate.

7. The apparatus of claim 1, wherein the conductive patterned layer comprises Ti, and the resistive layer comprises $TiO_2$.

8. The apparatus of claim 1, wherein the conductive patterned layer assists in electroplating the palladium nanoparticles onto the conductive patterned layer.

9. The apparatus of claim 1, wherein the nanoparticles comprise palladium-silver nanoparticles.

10. An apparatus for sensing hydrogen comprising:
a substrate comprising an insulating material;
a conductive patterned layer having a side-wall deposited on the substrate; and
a palladium nanowire deposited to the side-wall, wherein the conductive patterned layer is oxidized to form a resistive layer, wherein a portion of the nanowire and a portion of the resistive path form at least one conductive path in the presence of hydrogen and lack a conductive path in the absence of hydrogen.

11. The apparatus of claim 10, wherein the conductive patterned layer comprises Ti, and the resistive layer comprises $TiO_2$.

12. The apparatus of claim 10, wherein the nanoparticles comprise palladium-silver nanoparticles.

* * * * *